(12) United States Patent
Kozawa et al.

(10) Patent No.: US 8,329,909 B2
(45) Date of Patent: Dec. 11, 2012

(54) METHOD FOR PRODUCING 2-AZAADAMANTANE COMPOUND FROM BICYCLOCARBAMATE COMPOUND

(75) Inventors: Masami Kozawa, Funabashi (JP); Yuki Endo, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 0 days.

(21) Appl. No.: 13/265,978

(22) PCT Filed: Apr. 23, 2010

(86) PCT No.: PCT/JP2010/057278
§ 371 (c)(1),
(2), (4) Date: Oct. 24, 2011

(87) PCT Pub. No.: WO2010/123115
PCT Pub. Date: Oct. 28, 2010

(65) Prior Publication Data
US 2012/0053348 A1    Mar. 1, 2012

(30) Foreign Application Priority Data
Apr. 24, 2009    (JP) .................................. 2009-105926

(51) Int. Cl.
*C07D 215/38*    (2006.01)
(52) U.S. Cl. ......... 546/131; 546/124; 546/127; 546/129
(58) Field of Classification Search .................. 546/131, 546/129, 127, 124
See application file for complete search history.

(56) References Cited

U.S. PATENT DOCUMENTS
2010/0311977 A1 * 12/2010 Hamada et al. .................. 546/94

FOREIGN PATENT DOCUMENTS
WO    2009 066735    5/2009

OTHER PUBLICATIONS

Staas et. al., "Synthesis and Reactions of 4-Substituted 2-Azaadamantanes", J. Org. Chem., vol. 39, No. 2, 1974.*
Papageorgiou et. al., "Selective Hydrogenolysis of Novel Benzyl Carbamate Protecting Groups", Organic Letters, 2000, vol. 2, No. 8, pp. 1049-1051.*
Salvatore, et. al., "Synthesis of secondary amines" Tetrahedron 57 (2001) pp. 7785-7811.*
Greene T, Wuts P. Protective Groups in Organic Synthesis [e-book]. John Wiley & Sons, Inc. (US); 1999. Available from: eBook Collection (EBSCOhost), Ipswich, MA. Accessed Jan. 1, 2012.*
Staas, W. H. et al., "Synthesis and Reactions of 4-Substituted 2-Azaadamantanes", Journal of Organic Chemistry, vol. 39, No. 26, pp. 3822-3827, (1974).
Greene, T. W. et al., "Protective Groups in Organic Synthesis", Third Edition, pp. 531-540, 552-555, (1999).
Henkel, J. G. et al., "Neighboring Group Effects in The β-Halo Amines. Synthesis and Solvolytic Reactivity of the Anti-4-Substituted 2-Azaadamantyl System", Journal of Organic Chemistry, vol. 46, No. 24, pp. 4953-4959, (1981).
Sasaki, T. et al., "Synthesis and Acidolysis of 3-Endo-Azidomethyl- and 3-Endo-Azidobicyclo [3.3.1] Non-6-Enes. A Novel Synthesis of 4-Azahomoadamant-4-Enes", Journal of the Chemical Society, Perkin Transactions, vol. 1, No. 10, pp. 2529-2534, (1983).
International Search Report Issued May 25, 2010 in PCT/JP10/057278 filed Apr. 23, 2010.

* cited by examiner

*Primary Examiner* — D M Seaman
(74) *Attorney, Agent, or Firm* — Oblon, Spivak, McClelland, Maier & Neustadt, L.L.P.

(57) ABSTRACT

To provide a novel method for producing a 2-azaadamantane compound from a bicyclocarbamate compound.
In accordance with the following scheme:

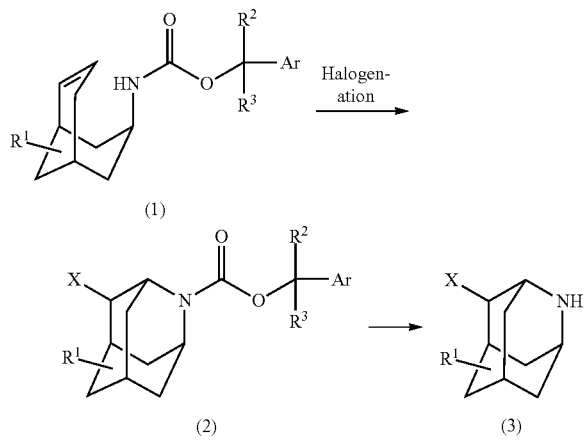

a bicyclocarbamate compound represented by the formula (1) is reacted with a halogenating agent to produce a 2-azaadamantane carbamate compound represented by the formula (2), and the 2-azaadamantane carbamate compound is subjected to hydrogenolysis to produce a 2-azaadamantane compound represented by the formula (3) (in the formulae, $R^1$ is hydrogen or the like, each of $R^2$ and $R^3$ which are independent of each other, is a hydrogen atom or a $C_{1-6}$ alkyl group, Ar is an aryl group which may be substituted by $R^a$, $R^a$ is halogen or the like, X is a halogen atom, and Y is X or a hydrogen atom).

20 Claims, No Drawings

METHOD FOR PRODUCING 2-AZAADAMANTANE COMPOUND FROM BICYCLOCARBAMATE COMPOUND

TECHNICAL FIELD

The present invention relates to a method for producing a 2-azaadamantane compound from a bicyclocarbamate compound.

BACKGROUND ART

2-Azaadamantane compounds are widely used e.g. as an oxidizing catalyst of an alcohol. As a method for producing 2-azaadamantane compounds, a method for producing N-acetyl-2-azaadamantane by reacting a N-acetylbicycloamine compound with a halogenating agent has been known (Non-Patent Document 1).

Further, for the purpose of obtaining a 2-azaadamantane compound, with respect to removal of an alkoxycarbonyl group from N-trichloroethoxycarbonyl-2-azaadamantane and N-dichloroethoxycarbonyl-2-azaadamantane, a method of using zinc has been studied (Non-Patent Document 2).

PRIOR ART DOCUMENTS

Non-Patent Documents

Non-Patent Document 1: J. Org. Chem. 1974, 39(26), 3822-3827

Non-Patent Document 2: J. Org. Chem. 1981, 46(24), 4953-4959

DISCLOSURE OF INVENTION

Technical Problem

With respect to a method for producing a 2-azaadamantane compound using a bicyclocarbamate compound as a substrate (material), the above Non-Patent Document 1 discloses that when a bicyclocarbamate compound is to be cyclized in the same manner, a lactone, not 2-azaadamantane, is formed.

Further, the above Non-Patent Document 2 discloses that when a bicyclocarbamate compound is used as a substrate, no aimed 2-azaadamantane can be obtained, and that although removal of a benzoyl group by alkali hydrolysis of N-benzoyl-2-azaadamantane has been studied, no aimed 2-azaadamantane compound can be obtained.

It is object of the present invention to provide a novel method for producing a 2-azaadamantane compound from a bicyclocarbamate compound as a substrate (material) with high efficiency.

Solution to Problem

The present inventors have conducted extensive studies to achieve the above object and as a result, found that a 2-azaadamantane compound can be produced efficiently by reacting a bicyclocarbamate compound having an aryl group, with a halogenating agent to produce a 2-azaadamantane carbamate compound, and then subjecting the 2-azaadamantane carbamate compound to hydrogenolysis, and accomplished the present invention.

Here, the 2-azaadamantane carbamate compound as an intermediate of the 2-azaadamantane compound is a novel compound which is not disclosed in any documents.

That is, the present invention provides the following.

[1] A method for producing a 2-azaadamantane compound represented by the following formula (3) or its salt:

wherein $R^1$ is as defined below, and Y is a hydrogen atom or a halogen atom; which comprises reacting a carbamate compound represented by the following formula (1):

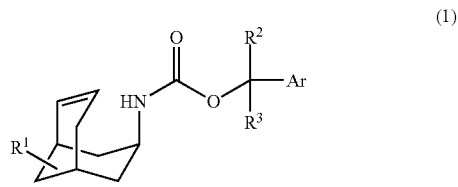

wherein $R^1$ is at least one substituent selected from the group consisting of a hydrogen atom, a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a linear or branched $C_{1-12}$ alkylcarbonyl group, a $C_{3-12}$ cycloalkylcarbonyl group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a (linear or branched $C_{1-12}$ alkyl)carbonyloxy group, a ($C_{3-12}$ cycloalkyl)carbonyloxy group, a (linear or branched $C_{1-12}$ alkyl)carbonylthio group, a ($C_{3-12}$ cycloalkyl)carbonylthio group, a (linear or branched $C_{1-12}$ alkyl)carbonylamino group, a ($C_{3-12}$ cycloalkyl)carbonylamino group, a di(linear or branched $C_{1-12}$ alkylcarbonyl)amino group, a di($C_{3-12}$ cycloalkylcarbonyl)amino group, a linear or branched $C_{1-6}$ haloalkyl group, a $C_{3-6}$ halocycloalkyl group, a linear or branched $C_{2-6}$ alkenyl group, a $C_{3-6}$ cycloalkenyl group, a linear or branched $C_{2-6}$ haloalkenyl group, a $C_{3-6}$ halocycloalkenyl group, a linear or branched $C_{2-6}$ alkynyl group, a linear or branched $C_{2-6}$ haloalkynyl group, a benzyl group which may be substituted by $R^a$, a benzyloxy group which may be substituted by $R^a$, a benzylthio group which may be substituted by $R^a$, a benzylamino group which may be substituted by $R^a$, a dibenzylamino group which may be substituted by $R^a$, a benzylcarbonyl group which may be substituted by $R^a$, a benzyloxycarbonyl group which may be substituted by $R^a$, a benzylthiocarbonyl group which may be substituted by $R^a$, a benzylaminocarbonyl group which may be substituted by $R^a$, a dibenzylaminocarbonyl group which may be substituted by $R^a$, a benzylcarbonyloxy group which may be substituted by $R^a$, a benzylcarbonylthio group which may be substituted by $R^a$, a benzylcarbonylamino group which may be substituted by $R^a$, a di(benzylcarbonyl)amino group which may be substituted by $R^a$, an aryl group which may be substituted by $R^a$, an aryloxy group which may be substituted by $R^a$, an arylthio group which may be substituted by $R^a$, an arylamino group which may be substituted by $R^a$, a diarylamino group which may be substituted by $R^a$, an arylcarbonyl group which may be substituted by $R^a$, an aryloxycarbonyl group which may be substituted by $R^a$, an arylthiocarbonyl group which may be substituted by $R^a$, an arylaminocarbonyl group which may be substituted by $R^a$, a diarylaminocarbonyl group which may be substituted by $R^a$, an arylcarbonyloxy group which may be substituted by $R^a$, an arylcarbonylthio group which may be substituted by $R^a$, an arylcarbonylamino group which may be substituted by $R^a$, and a di(arylcarbonyl)amino group which may be substituted by $R^a$, and when the number of substituents is two or more, the respective substituents may be the same or different;

$R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_{2-6}$ haloalkynylsulfonyl group, a nitro group, a cyano group, a formyl group, a hydroxy group, a mercapto group, an amino group, SCN, a $C_{1-6}$ alkyloxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di$C_{1-6}$ alkylamino group, the number of substituents $R^a$ is from 1 to 5, and when the number of $R^a$ is two or more, the respective substituents may be the same or different; and each of $R^2$ and $R^3$ which are independent of each other, is a hydrogen atom or a $C_{1-6}$ alkyl group, and Ar is an aryl group which may be substituted by $R^a$; with a halogenating agent to produce a 2-azaadamantane carbamate compound represented by the following formula (2):

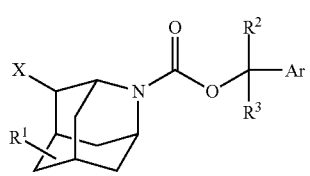

(2)

wherein Ar, $R^1$, $R^2$ and $R^3$ are as defined above, and X is a halogen atom; and subjecting the 2-azaadamantane carbamate compound to hydrogenolysis.

[2] A method for producing a 2-azaadamantane carbamate compound represented by the following formula (2):

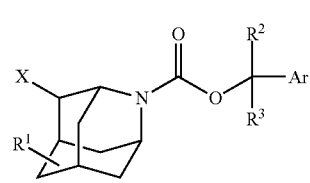

(2)

wherein Ar, $R^1$, $R^2$, $R^3$ and X are as defined in the above [1], which comprises reacting a carbamate compound represented by the following formula (1):

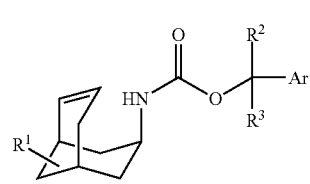

(1)

wherein $R^1$, $R^2$ and $R^3$ are as defined in the above [1], with a halogenating agent.

[3] A method for producing a 2-azaadamantane compound represented by the following formula (3) or its salt:

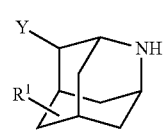

(3)

wherein $R^1$ and Y are as defined in the above [1], which comprises subjecting a 2-azaadamantane carbamate compound represented by the following formula (2) to hydrogenolysis.

[4] The production method according to the above [1], [2] or [3], wherein $R^1$ is at least one substituent selected from a hydrogen atom, a hydroxy group, an amino group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a benzyl group which may be substituted by $R^a$, an aryl group which may be substituted by $R^a$, an aryloxy group which may be substituted by $R^a$, an arylthio group which may be substituted by $R^a$, an arylamino group which may be substituted by $R^a$, and a diarylamino group which may be substituted by $R^a$, and when the number of substituents is two or more, the respective substituents may be the same or different; and $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a hydroxy group, an amino group, a phenyl group, a $C_{1-6}$ alkylamino group or a $diC_{1-6}$ alkylamino group, the number of substituents $R^a$ is from 1 to 5, and when the number of $R^a$ is two or more, the respective substituents may be the same or different.

[5] The production method according to the above [1], [2] or [3], wherein $R^1$ is a hydrogen atom.

[6] A 2-azaadamantane carbamate compound represented by the following formula (2):

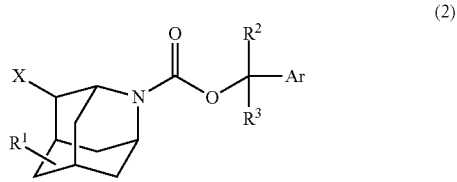

(2)

wherein Ar, $R^1$, $R^2$ and $R^3$ are as defined in the above [1], and X is a halogen atom.

[7] The 2-azaadamantane carbamate compound according to the above [6], wherein $R^1$ is a hydrogen atom.

Advantageous Effects of Invention

According to the present invention, a 2-azaadamantane compound which is useful as e.g. a precursor of 2-azaadamantane-N-oxyl (AZADO) used as an oxidizing catalyst of an alcohol, can efficiently be produced with a high yield.

DESCRIPTION OF EMBODIMENT

The halogen atom in this specification may be a fluorine atom, a chlorine atom, a bromine atom or an iodine atom. An expression "halo" in this specification also represents such a halogen atom.

An expression "$C_{a-b}$ alkyl" in this specification represents a linear or branched hydrocarbon group having from a to b carbon atoms; for example, a methyl group, an ethyl group, a n-propyl group, an i-propyl group, a n-butyl group, an i-butyl group, a s-butyl group, a t-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, a n-hexyl group, a 1-methylpentyl group, a 2-methylpentyl group, a 1,1-dimethylbutyl group, a 1,3-dimethylbutyl group, a heptyl group, an octyl group, a nonyl group, a decyl group, an undecyl group, a dodecyl group, etc. are mentioned as its specific examples; and it is selected within the range of the specified number of carbon atoms.

An expression "$C_{a-b}$ haloalkyl" in this specification represents a linear or branched hydrocarbon group having from a to b carbon atoms, wherein any hydrogen atoms bonded to the carbon atoms are optionally substituted by halogen atoms. In such a case, when hydrogen atoms are substituted by two or more halogen atoms, such halogen atoms may be the same or different from one another. For example, a fluoromethyl group, a chloromethyl group, a bromomethyl group, an iodomethyl group, a difluoromethyl group, a chlorofluoromethyl group, a dichloromethyl group, a bromofluoromethyl group, a trifluoromethyl group, a chlorodifluoromethyl group, a dichlorofluoromethyl group, a trichloromethyl group, a bromodifluoromethyl group, a bromochlorofluoromethyl group, a dibromofluoromethyl group, a 2-fluoroethyl group, a 2-chloroethyl group, a 2-bromoethyl group, a 2,2-difluoroethyl group, a 2-chloro-2-fluoroethyl group, a 2,2-dichloroethyl group, a 2-bromo-2-fluoroethyl group, a 2,2,2-trifluoroethyl group, a 2-chloro-2,2-difluoroethyl group, a 2,2-dichloro-2-fluoroethyl group, a 2,2,2-trichloroethyl group, a 2-bromo-2,2-difluoroethyl group, a 2-bromo-2-chloro-2-fluoroethyl group, a 2-bromo-2,2-dichloroethyl group, a 1,1,2,2-tetrafluoroethyl group, a pentafluoroethyl group, a 1-chloro-1,2,2,2-tetrafluoroethyl group, a 2-chloro-1,1,2,2-tetrafluoroethyl group, a 1,2-dichloro-1,2,2-trifluoroethyl group, a 2-bromo-1,1,2,2,-tetrafluoroethyl group, a 2-fluoropropyl group, a 2-chloropropyl group, a 2-bromopropyl group, a 2-chloro-2-fluoropropyl group, a 2,3-dichloropropyl group, a 2-bromo-3-fluoropropyl group, a 3-bromo-2-chloropropyl group, a 2,3-dibromopropyl group, a 3,3,3-trifluoropropyl group, a 3-bromo-3,3-difluoropropyl group, a 2,2,3,3-tetrafluoropropyl group, a 2-chloro-3,3,3-trifluoropropyl group, a 2,2,3,3,3-pentafluoropropyl group, a 1,1,2,3,3,3-hexafluoropropyl group, a heptafluoropropyl group, a 2,3-dichloro-1,1,2,3,3-pentafluoropropyl group, a 2-fluoro-1-methylethyl group, a 2-chloro-1-methylethyl group, a 2-bromo-1-methylethyl group, a 2,2,2-trifluoro-1-(trifluoromethyl)ethyl group, a 1,2,2,2,-tetrafluoro-1-(trifluoromethyl)ethyl group, a 2,2,3,3,4,4-hexafluorobutyl group, a 2,2,3,4,4,4-hexafluorobutyl group, a 2,2,3,3,4,4,4-heptafluorobutyl group, a 1,1,2,2,3,3,4,4-octafluorobutyl group, a nonafluorobutyl group, a 4-chloro-1,1,2,2,3,3,4,4-octafluorobutyl group, a 2-fluoro-2-methylpropyl group, a 2-chloro-1,1-dimethylethyl group, a 2-bromo-1,1-dimethylethyl group, a 5-chloro-2,2,3,4,4,5,5,-heptafluoropentyl group, a tridecafluorohexyl group, etc. are mentioned as its specific examples, and it is selected within the range of the specified number of carbon atoms.

An expression "$C_{a-b}$ cycloalkyl" in this specification represents a cyclic hydrocarbon group having from a to b carbon atoms and can form a 3- to 6-membered single ring or condensed ring structure. Further, each ring may be optionally substituted by an alkyl group within the range of the specified number of carbon atoms. For example, a cyclopropyl group, a 1-methylcyclopropyl group, a 2-methylcyclopropyl group, a 2,2-dimethylcyclopropyl group, a 2,2,3,3-tetramethylcyclopropyl group, a cyclobutyl group, a cyclopentyl group, a 2-methylcyclopentyl group, a 3-methylcyclopentyl group, a cyclohexyl group, a 2-methylcyclohexyl group, a 3-methylcyclohexyl group, a 4-methylcyclohexyl group, a bicyclo[2.2.1]heptane-2-yl group, etc. are mentioned as its specific examples, and it is selected within the range of the specified number of carbon atoms.

An expression "$C_{a-b}$ halocycloalkyl" in this specification represents a cyclic hydrocarbon group having from a to b carbon atoms, wherein any hydrogen atoms bonded to the carbon atoms are optionally substituted by halogen atoms and can form a 3- to 6-membered single ring or condensed ring structure. Further, each ring may optionally be substituted by an alkyl group within the range of the specified number of carbon atoms, and the substitution by the halogen atoms may be at the ring-structure portion or side chain portion, or at both portions. Further, in a case where hydrogen atoms are substituted by two or more halogen atoms, such halogen atoms may be the same or different from one another. For example, a 2,2-difluorocyclopropyl group, a 2,2-dichlorocyclopropyl group, a 2,2-dibromocyclopropyl group, a 2,2-difluoro-1- methylcyclopropyl group, a 2,2-dichloro-1-methylcyclopropyl group, a 2,2-dibromo-1-methylcyclopropyl group, a 2,2,3,3-tetrafluorocyclobutyl group, a 2-(trifluoromethyl)cyclohexyl group, a 3-(trifluoromethyl)cyclohexyl group, a 4-(trifluoromethyl)cyclohexyl group, etc. are mentioned as its specific examples, and it is selected within the range of the specified number of carbon atoms.

An expression "$C_{a-b}$ alkenyl" in this specification represents a linear or branched unsaturated hydrocarbon group having from a to b carbon atoms and having one or more double bonds in its molecule; for example, a vinyl group, a 1-propenyl group, a 2-propenyl group, a 1-methylethenyl group, a 2-butenyl group, a 1-methyl-2-propenyl group, a 2-methyl-2-propenyl group, a 2-pentenyl group, a 2-methyl-2-butenyl group, a 3-methyl-2-butenyl group, a 2-ethyl-2-propenyl group, a 1,1-dimethyl-2-propenyl group, a 2-hexenyl group, a 2-methyl-2-pentenyl group, a 2,4-dimethyl-2,6-heptadienyl group, a 3,7-dimethyl-2,6-octadienyl group, etc. are mentioned as its specific examples; and it is selected within the range of the specified number of carbon atoms.

An expression "$C_{a-b}$ haloalkenyl" in this specification represents a linear or branched unsaturated hydrocarbon group having from a to b carbon atoms and having one or more double bonds in its molecule, wherein any hydrogen atoms bonded to the carbon atoms are optionally substituted by halogen atoms. In such a case, when hydrogen atoms are substituted by two or more halogen atoms, such halogen atoms may be the same or different from one another. For example, 2,2-dichlorovinyl group, a 2-fluoro-2-propenyl group, a 2-chloro-2-propenyl group, a 3-chloro-2-propenyl group, a 2-bromo-2-propenyl group, a 3-bromo-2-propenyl group, a 3,3-difluoro-2-propenyl group, a 2,3-dichloro-2-propenyl group, a 3,3-dichloro-2-propenyl group, a 2,3-dibromo-2-propenyl group, a 2,3,3-trifluoro-2-propenyl group, a 2,3,3-trichloro-2-propenyl group, a 1-(trifluoromethyl)ethenyl group, a 3-chloro-2-butenyl group, a 3-bromo-2-butenyl group, a 4,4-difluoro-3-butenyl group, a 3,4,4-trifluoro-3-butenyl group, a 3-chloro-4,4,4-trifluoro-2-butenyl group, a 3-bromo-2-methyl-2-propenyl group, etc. are mentioned as its specific examples, and it is selected within the range of the specified number of carbon atoms.

An expression "$C_{a-b}$ cycloalkenyl" in this specification represents a cyclic unsaturated hydrocarbon group having from a to b carbon atoms and having one or more double bonds, and can form a 3- to 6-membered single ring or condensed ring structure. Further, each ring may optionally be substituted by an alkyl group within the range of the specified number of carbon atoms, and further, the double bond may be endo- or exo-. For example, 2-cyclopenten-1-yl group, a 3-cyclopenten-1-yl group, a 2-cyclohexen-1-yl group, a 3-cyclohexen-1-yl group, a bicyclo[2.2.1]-5-hepten-2-yl group, etc. are mentioned as its specific examples, and it is selected within the range of the specified number of carbon atoms.

An expression "$C_{a-b}$ halocycloalkenyl" in this specification represents a cyclic unsaturated hydrocarbon group having from a to b carbon atoms and having one or more double bonds, wherein any hydrogen atoms bonded to the carbon atoms are optionally substituted by halogen atoms, and can form a 3- to 6-membered single ring or condensed ring structure. Further, each ring may optionally be substituted by an alkyl group within the range of the specified number of carbon atoms, and further, the double bond may be endo- or exo-. Further, the substitution by halogen atoms may be at the ring structure portion or side chain portion, or at both portions, and when hydrogen atoms are substituted by two or more halogen atoms, such halogen atoms may be the same or different from one another. For example, a 2-chlorobicyclo[2.2.1]-5-hepten-2-yl group, etc. are mentioned as its specific examples, and it is selected within the range of the specified number of carbon atoms.

An expression "$C_{a-b}$ alkynyl" in this specification represents a linear or branched unsaturated hydrocarbon group having from a to b carbon atoms and having one or more triple bonds in its molecule. For example, an ethynyl group, a 1-propynyl group, a 2-propynyl group, a 2-butynyl group, a 1-methyl-2-propynyl group, a 2-pentynyl group, a 1-methyl-2-butynyl group, a 1,1-dimethyl-2-propynyl group, a 2-hexynyl group, etc. are mentioned as its specific examples, and it is selected within the range of specified number of carbon atoms.

An expression "$C_{a-b}$ haloalkynyl" in this specification represents a linear or branched unsaturated hydrocarbon group having from a to b carbon atoms and having one or more triple bonds in its molecule, wherein any hydrogen atoms bonded to the carbon atoms are optionally substituted by halogen atoms. In such a case, when hydrogen atoms are substituted by two or more halogen atoms, such halogen atoms may be the same or different from one another. For example, a 2-chloroethynyl group, a 2-bromoethynyl group, a 2-iodoethynyl group, a 3-chloro-2-propynyl group, a 3-bromo-2-propynyl group, a 3-iodo-2-propynyl group, etc. are mentioned as its specific examples, and it is selected within the range of the specific number of carbon atoms.

The aryl group which may be substituted by $R^a$ may, for example, be a phenyl group, an o-methylphenyl group, a m-methylphenyl group, a p-methylphenyl group, an o-chlorophenyl group, a m-chlorophenyl group, a p-chlorophenyl group, an o-fluorophenyl group, a p-fluorophenyl group, an o-methoxyphenyl group, a p-methoxyphenyl group, a p-nitrophenyl group, a p-cyanophenyl group, an α-naphthyl group, a β-naphthyl group, an o-biphenylyl group, a m-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 2-thienyl group, a 3-thienyl group, a 2-furyl group, a 3-furyl group, a 2-pyranyl group, a 3-pyranyl group, a 4-pyranyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyradinyl group, a 2-pyrimidinyl group, a 4-pyrimidinyl group, a 5-pyrimidinyl group, a 3-pyridazinyl group, a 4-pyridazinyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, a 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 2-naphthyridinyl group, a 3-naphthyridinyl group, a 4-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-ptenidinyl group, a 4-ptenidinyl group, a 6-ptenidinyl group, a 7-ptenidinyl group or a 3-furazanyl group, and the benzyl group which may be substituted by $R^a$ may, for example, be a benzyl group, an o-methylbenzyl group, a m-methylbenzyl group, a p-methylbenzyl group, an o-chlorobenzyl group, a m-chlorobenzyl group, a p-chlorobenzyl group, an o-fluorobenzyl group, a p-fluorobenzyl group, an o-methoxybenzyl group, a p-methoxybenzyl group, a p-nitrobenzyl group, or a p-cyanobenzyl group.

As preferred $R^1$, for example, a hydrogen atom, a hydroxy group, an amino group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl) amino group, a di(linear or branched $C_{1-6}$ alkyl)amino group, a di($C_{3-6}$ cycloalkyl)amino group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a benzyl group which may be substituted by $R^a$, an aryl group which may be substituted by $R^a$, an aryloxy group which may be substituted by $R^a$, an arylthio group which may be substituted by $R^a$, an arylamino group which may be substituted by $R^a$, or a diarylamino group which may be substituted by $R^a$, may be mentioned, and particularly preferably, for example, a hydrogen atom may be mentioned.

As preferred $R^a$, for example, a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a hydroxy group, an amino group, a phenyl group, a $C_{1-6}$ alkylamino group or a di$C_{1-6}$ alkylamino group may be mentioned, and particularly preferably, for example, a hydrogen atom, a halogen atom or an alkyl group may be mentioned.

As preferred $R^2$ and $R^3$, for example, a hydrogen atom may be mentioned.

As preferred Ar, for example, a phenyl group may be mentioned.

As preferred Y, for example, a hydrogen atom may be mentioned.

The present invention can be carried out, for example, in accordance with the following scheme:

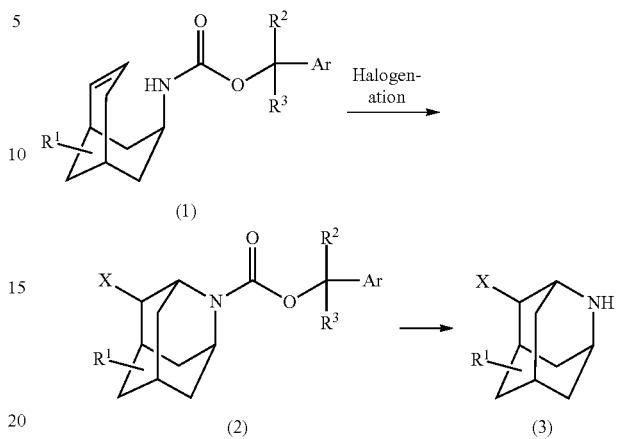

(In the formulae, Ar, X, Y, $R^1$, $R^2$ and $R^3$ are as defined above.)

A step of reacting the compound of the formula (1) with a halogenating agent to obtain the compound of the formula (2) will be described below.

The halogenating agent is preferably chlorine, bromine, iodine, N-chlorosuccinimide, N-bromosuccinimide, N-iodosuccinimide, 1,3-dibromo-5,5-dimethylhydantoin, thionyl chloride, sulfuryl chloride, phosphorus oxychloride or the like.

The amount of the halogenating agent used is from 1 mol to 10 mol, preferably, for example, from 1 mol to 2 mol, per 1 mol of the compound (1) as the substrate.

In addition to the halogenating agent, preferably an inorganic or organic base can be used. Such a base is preferably potassium carbonate or sodium hydroxide. The amount of the base used is preferably from 0.01 molar time to 100 molar times, particularly preferably from 0.5 molar times to 2 molar times based on the compound (1).

The reaction temperature is from −40° C. to 200° C., and particularly, for example, preferably from −10° C. to 100° C., further preferably from −10° C. to 30° C. The reaction may be carried out at room temperature.

The reaction time is not necessarily constant depending on the substrate and the reaction conditions to be employed, and is usually from 1 minute to 100 hours, preferably from 5 minutes to 24 hours.

The reaction solvent is not particularly limited so long as it is inactive to the reaction, and for example, an alcohol such as methanol, ethanol, isopropyl alcohol or benzyl alcohol, a glycol such as ethylene glycol or propylene glycol, an ether such as ethyl, dioxane, tetrahydrofuran or methylcellosolve, an aliphatic hydrocarbon such as hexane or cyclohexane, an aromatic hydrocarbon such as benzene, an ester such as ethyl acetate or butyl acetate, or an aprotic polar solvent such as acetonitrile or N,N-dimethylformamide may be used.

The amount of the reaction solvent used is not particularly limited so long as it is sufficient to suspend or completely dissolve the material, and is usually from 0.5 to 10 times by weight based on the material.

Now, the method of subjecting the compound (2) to hydrogenolysis to produce the compound (3) will be described.

For the above hydrogenolysis, a reduction catalyst is preferably used, and as the reduction catalyst, a metal catalyst which is commonly used for catalytic reduction, for example, nickel, palladium, platinum, rhodium, ruthenium, cobalt or copper may be used. It is industrially preferred to use a palladium catalyst. Such a catalyst may be used in a metal state, but is usually used as supported on the surface of a support such as carbon, barium sulfate, silica gel, alumina or celite, and nickel, cobalt, copper or the like may be used also as a Raney catalyst. The amount of the catalyst used is not particularly limited, and usually, it is within a range of from 0.001 to 50 wt %, preferably from 0.01 to 5 wt %, as the weight of the metal catalyst based on the compound represented by the formula (2).

The reaction solvent is not particularly limited so long as it is inactive to the reaction, and for example, an alcohol such as methanol, ethanol or isopropyl alcohol, a glycol such as ethylene glycol or propylene glycol; an ether such as ether, dioxane, tetrahydrofuran or methylcellosolve; an aliphatic hydrocarbon such as hexane or cyclohexane; an aromatic hydrocarbon such as benzene, toluene or xylene; an ester such as ethyl acetate or butyl acetate; or an aprotic polar solvent such as acetonitrile or N,N-dimethylformamide may be used. In a case where a reaction solvent immiscible with water is used, if the reaction progress is slow, the progress of the reaction can be accelerated by adding an commonly used phase-transfer catalyst such as a quaternary ammonium salt or a quaternary phosphonium salt.

The amount of the reaction solvent used is not particularly limited so long as it is sufficient to suspend or completely dissolve the material, and is usually from 0.5 to 10 times by weight based on the material. The reaction temperature is not particularly limited. It is usually within a range of from 20 to 200° C., particularly preferably from 20 to 100° C. Further, the reaction pressure is usually at a level of from normal pressure to 50 atm. The reaction is usually carried out by adding a catalyst in a state where the material is dissolved or suspended in the solvent, and then introducing hydrogen at a predetermined temperature with stirring to carry out the reduction reaction. Completion of the reaction can be determined by the amount of hydrogen absorption or by thin layer chromatography or high performance liquid chromatography.

For the hydrogenolysis, preferably an inorganic or organic base can be present. Such a base is preferably triethylamine, potassium carbonate or sodium hydroxide. The amount of the base is preferably from 0.01 molar time to 100 molar times, particularly preferably from 1 molar time to 8 molar times, based on the compound (2).

Further, as a hydrogen source in the hydrogenolysis, for example, hydrogen is preferred, and in addition, e.g. ammonium formate or hydrazine may also be used.

In the production method of the present invention, substituents $R^1$ and $R^a$ include substituents which change before and after the reaction, and such substituents are included in the substituents $R^1$ and $R^a$ even after the reaction. Further, in such a case also, the formed 2-azaadamantane compound is still useful, and the effects of the present invention can be sufficiently achieved, and accordingly the selectivity of such substituents is not necessarily required.

The compound represented by the formula (1) as a starting material in the production method of the present invention can be produced in accordance with the following scheme from a 2-adamantanone derivative (4) as a starting material:

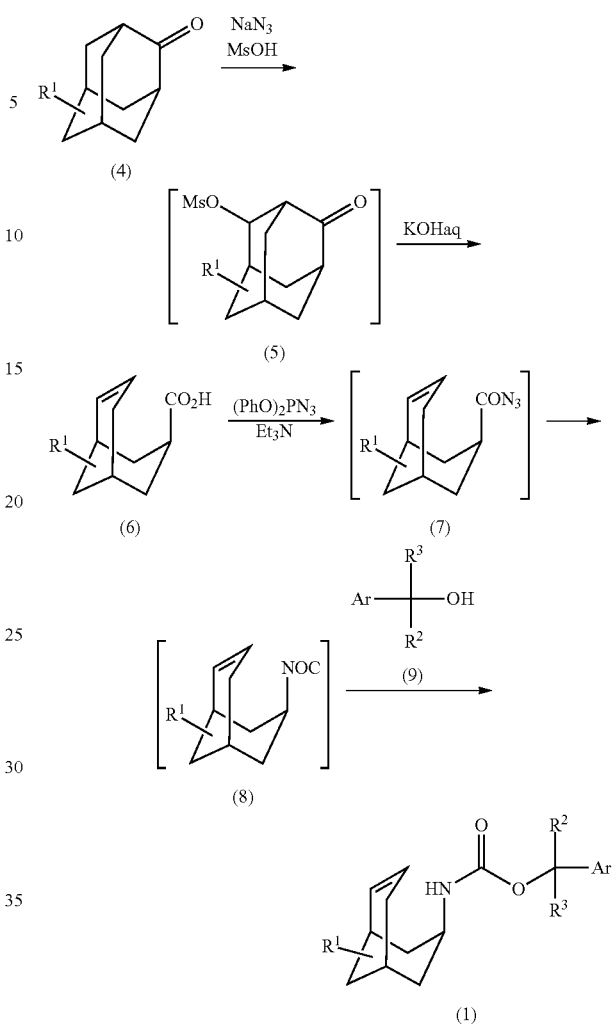

(In the formulae, Ms represents a methanesulfonyl group, and Ar, $R^1$, $R^2$ and $R^3$ are as defined above.)

The carboxylic acid compound represented by the formula (6) can be produced, for example, in accordance with J. Org. Chem., Vol. 39, No. 26, p. 3822 (1974).

After the compound (4) is led to the compound (5), the compound (6) may be produced in one step without isolating the compound (5). In such a case, for example, after the reaction from the compound (4) to the compound (5) is carried out, an aqueous solution of an alkali metal hydroxide is added to the reaction liquid to obtain the compound (6).

Conditions for production of the compound (1) from the compound (6) are in accordance with the method disclosed in J. Chem. Soc. Perkin Trans. I, p. 2529 (1983).

The alcohol (9) used in the reaction from the compound (8) to the compound (1) is used in an amount of usually from 0.1 equivalent amount to 100 equivalent amounts, preferably from 1 equivalent amount to 20 equivalent amounts based on the compound (8).

After the compound (6) is led to the compound (8), the compound (1) may be produced from the compound (6) in one step without isolation of the compound (8).

Further, the compound represented by the formula (1) may also be obtained by leading the compound represented by the formula (6) to the compound represented by the formula (10) as described below, followed by a known amino group protecting means.

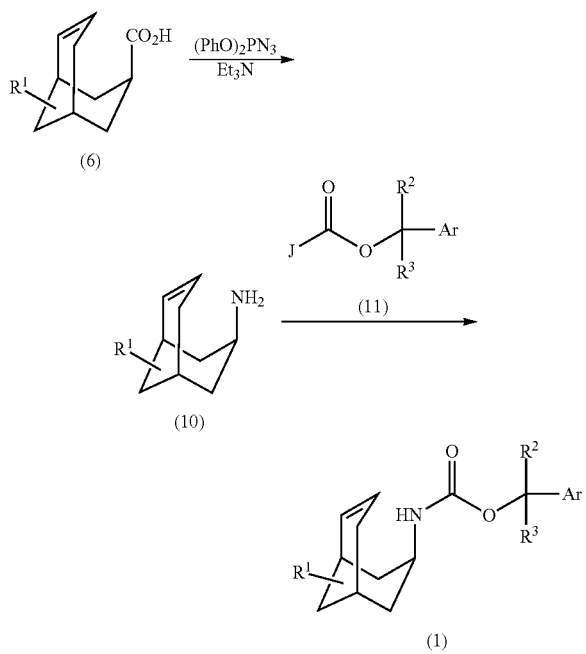

(In the formulae, Ar, $R^1$, $R^2$ and $R^3$ are as defined above, and J is a leaving group such as a halogen atom.)

As a means of reacting the compound represented by the formula (10) with the compound represented by the formula (11) to convert it to the compound represented by the formula (1), a known means of protecting an amino group may be employed. Such a means may, for example, be a method as disclosed in Protective Groups in Organic Chemistry (J. F. W. McOmie et al., Plenum Press; Protective Groups in Organic Synthesis, 3rd Edition (Theodora W. Greene, Peter G. M. Wuts, John Wiley & Sons, Inc. (ISBN:0-471-16019-9), April 1999.

The amount of the compound (11) used is in accordance with the above condition.

The solvent used in the reaction in each step is preferably one which is stable under the reaction conditions and which is inactive so as not to inhibit the reaction. Such a solvent may, for example, be water, an alcohol (such as methanol, ethanol, propanol, butanol or octanol), a cellosolve (such as methoxyethanol or ethoxyethanol), an aprotic polar organic solvent (such as dimethylformamide, dimethylsulfoxide, dimethylacetamide, tetramethylurea, sulfolane, N-methylpyrrolidone or N,N-dimethylimidazolidinone), an ether (such as diethyl ether, diisopropyl ether, t-butyl methyl ether, tetrahydrofuran or dioxane), an aliphatic hydrocarbon (such as pentane, hexane, c-hexane, octane, decane, decalin or petroleum ether), an aromatic hydrocarbon (such as benzene, chlorobenzene, o-dichlorobenzene, nitrobenzene, toluene, xylene, mesitylene or tetralin), a halogenated hydrocarbon (such as chloroform, dichloromethane, dichloroethane or carbon tetrachloride), a ketone (such as acetone, methyl ethyl ketone, methyl butyl ketone or methyl isobutyl ketone), a lower fatty acid ester (such as methyl acetate, ethyl acetate, butyl acetate or methyl propionate), an alkoxyalkane (such as dimethoxyethane or diethoxyethane), or a nitrile (such as acetonitrile, propionitrile or butyronitrile). Such solvents are properly selected in accordance with occurrence of the reaction, and they are used alone or as mixed. Further, as the case requires, they are used as a non-aqueous solvent by use of a proper dehydrating agent or drying agent. The above-described solvents are mere example to carry out the present invention, and the present invention is not limited to such conditions.

The desired product in each step may be purified by means of a usual purification means such as extraction, distillation, recrystallization or column chromatography, or it may be supplied as a starting material for the next step as a crude product without purification.

From the 2-azaadamantane compound obtained by the production method of the present invention, by oxidation for example, an AZADO derivative useful as an oxidizing catalyst of an alcohol can be produced.

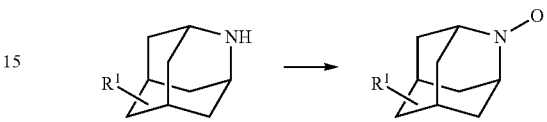

Now, the present invention will be described in detail with reference to Examples, but it should be understood that the present invention is by no means thereby restricted.

EXAMPLES

Starting Material Preparation Example 1

Preparation of endo-bicyclo[3.3.1]non-6-ene-3-carboxylic acid

Into a 1 L (liter) three-necked flask, 48.0 g (0.320 mol) of 2-adamantanone and 300 g (202 mL, 1.58 M) of methanesulfonic acid were added and dissolved. To this solution, 22.9 g (0.353 mol) of sodium azide was gradually added with stirring so that the temperature of the reaction solution was maintained to be from 20° C. to 35° C. In the process, hydrazoic acid and nitrogen gas were generated, and the reaction temperature was optionally lowered by cooling with ice or water bath. Thereafter, stirring was carried out at room temperature for one hour, and disappearance of 2-adamantanone was confirmed by gas chromatography. At that time, formation of 4-methanesulfonyl-2-adamantanone was confirmed.

Then, a Dimroth condenser was connected to the reaction apparatus, and a 50 mass % potassium hydroxide aqueous solution (450 mL) was gradually added. At that time, the reaction temperature rose to 95° C. The reaction solution was left to cool with stirring as it was at room temperature for 1.5 hours, and then, the reaction solution was washed with 600 mL of diethyl ether. To the aqueous layer, 120 mL of concentrated hydrochloric acid was carefully added to acidify the reaction solution, whereby the desired product was crystallized. It was collected by filtration, thoroughly washed with water and then dried to obtain 36.5 g (0.220 mol, 69%) of crude endo-bicyclo[3.3.1]non-6-ene-3-carboxylic acid.

Endo-bicyclo[3.3.1]non-6-ene-3-carboxylic acid: $^1$H-NMR (400 MHz, $CDCl_3$): d 5.65 (m, 1H), 5.58 (dt, J=9.5, 3.2 Hz, 1H), 2.57 (t, J=6.3 Hz, 1H), 2.39 (d, J=14.0 Hz, 1H), 2.36-2.20 (m, 4H), 2.06 (br s, 1H), 1.78-1.66 (m, 3H), 1.54 (br d, J=12.3 Hz, 1H). $^{13}$C-NMR (100 MHz, $CDCl_3$): d 182.6, 130.6, 129.5, 35.9, 31.9, 31.4, 31.1, 29.8, 28.5, 26.2. IR (neat, $cm_{-1}$): 1680. MS m/z: 166 ($M_+$), 79 (100%). HRMS (EI): Calcd. for $C_{10}H_{14}O_2$ 166.0994 ($M_+$). found: 166.0989.

Starting Material Preparation Example 2

Preparation of N-benzyloxycarbonyl-endo-bicyclo [3.3.1]non-6-en-3-ylamine

To a tetrahydropyran solution (88.5 mL, 1.0 M, 1 L round-bottomed flask) of endo-bicyclo[3.3.1]non-6-ene-3-carboxylic acid (14.7 g (88.5 mmol)), 29.8 mL (213 mmol) of triethylamine and 21.0 mL (97.4 mmol) of diphenylphosphoryl azide (DPPA) were sequentially added at room temperature, followed by stirring for 3 hours at the same temperature. At that time, endo-bicyclo[3.3.1]non-6-ene-3-carboxylic acid azide was formed in the reaction system.

To this reaction solution, 88.5 mL of tetrahydropyran and 91.6 mL (885 mmol) of benzyl alcohol were added, followed by heating and refluxing until disappearance of endo-bicyclo [3.3.1]non-6-ene-3-carboxyhydrazide was confirmed. After the reaction solution was left to cool, water and ethyl acetate were added for liquid separation. The organic layer was washed with a saturated sodium chloride aqueous solution, dried over magnesium sulfate and concentrated. The crude product was subjected to column chromatography (eluent: ethyl acetate/hexane (1:8 v/v)) to obtain 20.4 g (85%) of N-benzyloxycarbonyl-endo-bicyclo[3.3.1]non-6-en-3-ylamine.

N-benzyloxycarbonyl-endo-bicyclo[3.3.1]non-6-en-3-ylamine: $^1$H-NMR (400 MHz, CDCl$_3$): d 7.38-7.25 (m, 5H), 6.05 (t, J=7.8 Hz, 1H), 5.92 (d, J=8.4 Hz, 1H), 5.79 (dt, J=9.9, 3.2 Hz, 1H), 5.56 (dd, J=18.5, 12.4 Hz, 2H), 4.03 (m, 1H), 2.43 (dd, J=18.8, 7.2 Hz, 1H), 2.34 (br s, 1H), 2.18 (br s, 1H), 2.06 (br d, J=18.1 Hz 1H), 2.00 (dt, J=14.7, 5.5 Hz, 1H) 1.89-1.66 (m, 4H), 1.55 (br d, J=12.1 Hz, 1H). $_{13}$C-NMR (100 MHz, CDCl$_3$): d 155.5, 136.9, 134.4, 128.8, 128.4, 128.0, 127.9, 66.2, 44.7, 37.5, 34.2, 32.5, 31.0, 27.7, 25.5. IR (neat, cm$_{-1}$): 3434, 1721, 1504 MS m/z: 271 (M$_+$), 91 (100%). HRMS (EI): Calcd. for C$_{17}$H$_{21}$NO$_2$ 271.1572 (M$_+$). found: 271.1554.

Example 1

Preparation of
N-benzyloxycarbonyl-4-bromo-2-azaadamantane

To 5.0 g of N-benzyloxycarbonyl-endo-bicyclo[3.3.1]non-6-en-3-ylamine, 12.5 g of acetonitrile and 5.1 g of potassium carbonate were added and cooled to 0 to 10° C., and then a 50 wt % acetonitrile solution of 4.4 g of bromine was dropwise added over a period of 30 minutes. After stirring for 10 minutes, analysis by gas chromatography was carried out, whereupon the reaction was completed.

20 g of water was added, followed by stirring for about 30 minutes. Liquid separation was carried out, and the resulting organic layer was washed with 20 g of a 1N-NaOH aqueous solution and further washed with 20 g of water. The organic layer was concentrated to obtain 6.2 g of N-benzyloxycarbonyl-4-bromo-2-azaadamantane as an oil (yield: 96%).

N-benzyloxycarbonyl-4-bromo-2-azaadamantane $^1$H-NMR (300 MHz, CDCl$_3$): 1.5-2.8 (10H, m), 4.3-4.7 (3H, m), 5.15 (2H, s), 7.2-7.7 (5H, br)

Example 2

Preparation of 2-azaadamantane

To 1.0 g of N-benzyloxycarbonyl-4-bromo-2-azaadamantane, 10 g of toluene and 0.3 g of 10 wt % Pd/C (containing 50% of water) were charged, followed by stirring at 20 to 30° C. while 0.5 MPa of a hydrogen pressure was applied. The reaction was traced by gas chromatograph (GC), whereupon peaks of the starting material disappeared in 5 hours.

10 g of methanol was added, followed by stirring for 30 minutes, and then filtration by Celite (registered trademark by Celite Corporation) was carried out, followed by washing with 10 g of methanol twice. The filtrate and the liquid used for washing were put together and concentrated, and 10 g of toluene and 10 g of 1N hydrochloric acid were added. Liquid separation was carried out, and to the resulting aqueous layer, 10 g of toluene and 3 g of a 20 wt % NaOH aqueous solution were added, to extract 2-azaadamantane. The toluene layer was concentrated to obtain 0.3 g of a white solid (yield: 80%).

Example 3

Preparation of 2-azaadamantane

To 1.0 g of N-benzyloxycarbonyl-4-bromo-2-azaadamantane, 10 g of ethanol, 0.32 g of triethylamine and 0.5 g of 10 wt % Pd/C (containing 50% of water) were charged, followed by stirring at 20 to 30° C. for 5 hours while 0.5 MPa of a hydrogen pressure was applied. Filtration by Celite (registered trademark by Celite Corporation) was carried out to remove a solid, and the mother liquor was quantitatively analyzed, whereupon the yield of 2-azaadamantane was 85%.

Example 4

To 8.1 g of N-benzyloxycarbonyl-4-bromo-2-azaadamantane, 81 g of ethanol and 16.0 g of potassium carbonate were added, and 0.81 g of 10 wt % Pd/C (containing 50% of water) was charged, followed by stirring for 4 hours while 0.5 MPa of a hydrogen pressure was applied. Filtration by Celite was carried out to remove a solid, and the mother liquor was quantitatively analyzed, whereupon the yield of 2-azaadamantane was 80%.

Example 5

Preparation of
N-benzyloxycarbonyl-4-chloro-2-azaadamantane

To 110 mg (0.41 mmol) of N-benzyloxycarbonyl-endo-bicyclo[3.3.1]non-6-en-3-ylamine, 4.5 mL of acetonitrile and 101 mg (0.73 mmol) of potassium carbonate were added, and chlorine was bubbled under cooling with ice. 15 Minutes later, conversion of the starting material was confirmed by gas chromatography, and then 5 mL of water and 10 mL of toluene were added, followed by liquid separation. The resulting organic layer was washed with 5 mL of a 3% sodium thiosulfate aqueous solution, and further washed with 5 mL of water twice. The organic layer was concentrated to obtain 20 mg (0.39 mmol, 96%) of N-benzyloxycarbonyl-4-chloro-2-azaadamantane as a pale yellow solid.

N-benzyloxycarbonyl-4-chloro-2-azaadamantane $^1$H-NMR (300 MHz, CDCl3): 1.5-2.6 (10H, m), 4.0-4.6 (3H, m), 5.14 (2H, s), 7.1-7.7 (5H, m)

Reference Example 1

Preparation of 2-azaadamantane-N-oxyl (AZADO)

A methanol (31 ml, 0.5 M) and methylene chloride (10 ml) solution containing 9.7 g (70 mmol) of 2-azaadamantane and 2.6 g (7.75 mmol) of sodium tungstate dihydrate was stirred at room temperature for 3 hours. After completion of the reaction was confirmed, water (80 ml) was added and extraction with chloroform was carried out, and the resulting organic layer was dried over magnesium sulfate, and the solvent was distilled off under reduced pressure. The residue was subjected to silica gel column chromatography (eluent: ethyl acetate-hexane (1:8 v/v)), whereby from the eluate, AZADO (2.12 g, 13.9 mmol) was obtained as a red solid. Various data agreed with those of one prepared by a known preparation method.

Elemental analysis ($C_9H_{14}NO$) Calcd. for: C, 9.27; H, 71.02; N, 9.20. found: H, 9.18; C, 71.06; N, 9.13.

Sublimation point: 1,600 Pa, 48° C.

Structure determination of intermediate formed when 2-azaadamantane is prepared from N-benzyloxycarbonyl-4-bromo-2-azaadamantane

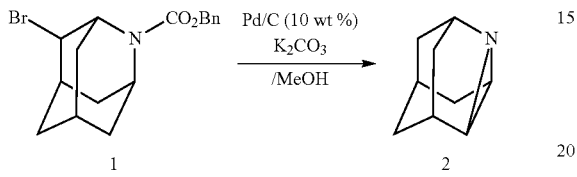

Experiment Method

To a reactor, 2.52 g (7.2 mmol) of N-benzyloxycarbonyl-4-bromo-2-azaadamantane 1, 25.2 g of MeOH, 4.98 g of $K_2CO_3$ (5 equivalent amounts based on 1) and 0.120 g (10 wt %) of 10 wt % Pd/C (containing 50% of water) were added, followed by stirring in a hydrogen atmosphere at 30° C. for 10 minutes. The reaction liquid was subjected to filtration, and the obtained reaction solution was concentrated to distill MeOH off. To the obtained residue, toluene was added, followed by washing with a 5% NaOH aqueous solution, and the organic layer was concentrated to obtain 0.95 g (6.9 mmol, yield: 96%) of compound 2 as a white solid.

Spectral Data of Compound 2

$^1$HNMR/(CDCl$_3$ [500 MHz]

δ=1.48 (dd, J=13.4, 4.15 Hz, 1H), δ=1.54 (s, 2H), δ=1.63 (dd, J=13.1, 2.75 Hz, 1H), δ=1.70 (dd, J=10.3, 1.85 Hz, 1H), δ=1.91 (s, 1H), δ=2.06 (dd, J=32.3, 13.3 Hz, 2H), δ=2.43-2.51 (mt, 3H), δ=2.56 (t, J=5.0 Hz, 1H), δ=3.55 (t, J=5.0 Hz, 1H)

$^{13}$C NMR/CDCl$_3$ [500 MHz] (dept135°)

δ=24.6 (CH), δ=28.8 (CH$_2$), δ=31.4 (CH), δ=31.8 (CH$_2$), δ=32.5 (CH$_2$), δ=41.8 (CH), δ=45.5 (C H), δ=50.2 (CH), δ=54.4 (CH$_2$)

HRMS (TOF): m/z: 135.10480 (100%), 136.10815 (9.7%)$_o$ Chemical Formula: $C_9H_{13}N$,

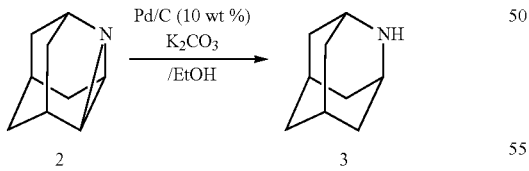

To a reactor, 221 mg (1.63 mmol) of compound 2, 2.2 g of EtOH, 1.13 g of $K_2CO_3$ and 27 mg of 10 wt % Pd/C (containing 50% of water) were added, followed by stirring in a hydrogen atmosphere at 30° C. for 15 hours. The reaction liquid was subjected to filtration, and the obtained reaction solution was concentrated to obtain a residue, to which toluene was added, followed by washing with a 5% NaOH aqueous solution, and the organic layer was concentrated to obtain 211 mg (1.54 mmol, yield: 94%) of 2-azaadamantane 3 as a white solid.

Industrial Applicability

A 2-azaadamantane compound efficiently produced from a bicyclocarbamate compound according to the present invention can be widely used e.g. as an alcohol oxidizing catalyst.

The entire disclosure of Japanese Patent Application No. 2009-105926 filed on Apr. 24, 2009 including specification, claims and summary is incorporated herein by reference in its entirety.

The invention claimed is:

1. A method for producing a 2-azaadamantane compound of formula (3) or its salt, the method comprising:

(A) reacting a carbamate compound of formula (1):

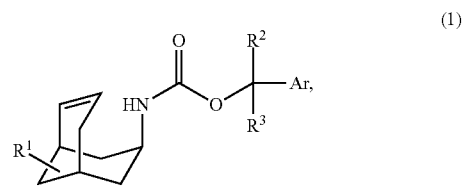

wherein $R^1$ is at least one substituent selected from the group consisting of a hydrogen atom, a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a linear or branched $C_{1-12}$ alkylcarbonyl group, a $C_{3-12}$ cycloalkylcarbonyl group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a (linear or branched $C_{1-12}$ alkyl)carbonyloxy group, a ($C_{3-12}$ cycloalkyl)carbonyloxy group, a (linear or branched $C_{1-12}$ alkyl)carbonylthio group, a ($C_{3-12}$ cycloalkyl)carbonylthio group, a (linear or branched $C_{1-12}$ alkyl)carbonylamino group, a ($C_{3-12}$ cycloalkyl)carbonylamino group, a di(linear or branched $C_{1-12}$ alkylcarbonyl)amino group, a di($C_{3-12}$ cycloalkylcarbonyl)amino group, a linear or branched $C_{1-6}$ haloalkyl group, a $C_{3-6}$ halocycloalkyl group, a linear or branched $C_{2-6}$ alkenyl group, a $C_{3-6}$ cycloalkenyl group, a linear or branched $C_{2-6}$ haloalkenyl group, a $C_{3-6}$ halocycloalkenyl group, a linear or branched $C_{2-6}$ alkynyl group, a linear or branched $C_{2-6}$ haloalkynyl group, a benzyl group which is optionally substituted by $R^a$, a benzyloxy group which is optionally substituted by $R^a$, a benzylthio group which is optionally substituted by $R^a$, a benzylamino group which is optionally substituted by $R^a$, a dibenzylamino group which is optionally substituted by $R^a$, a benzylcarbonyl group which is optionally substituted by $R^a$, a benzyloxycarbonyl group which is optionally substituted by $R^a$, a benzylthiocarbonyl group which is optionally substituted by $R^a$, a benzylaminocarbonyl group which is optionally substituted by $R^a$, a dibenzylaminocarbonyl group which is optionally substituted by $R^a$, a benzylcarbonyloxy group which is optionally substituted by $R^a$, a benzylcarbonylthio group which is optionally substituted by $R^a$, a benzylcarbonylamino group which is optionally substituted by $R^a$, a di(benzylcarbonyl)amino group which is optionally substituted by $R^a$, an aryl group which is optionally substituted by $R^a$, an aryloxy group which is optionally substituted by $R^a$, an arylthio group which is optionally substituted by $R^a$, an arylamino group which is optionally substituted by $R^a$, a diarylamino group which is optionally substituted by $R^a$, an arylcarbonyl group which is optionally substituted by $R^a$, an aryloxycarbonyl group which is optionally substituted by $R^a$, an arylthiocarbonyl group which is optionally substituted by $R^a$, an arylaminocarbonyl group which is optionally substituted by $R^a$, a diarylaminocarbonyl group which is optionally substituted by $R^a$, an arylcarbonyloxy group which is optionally substituted by $R^a$, an arylcarbonylthio group which is optionally substituted by $R^a$, an arylcarbonylamino group which is optionally substituted by $R^a$, and a di(arylcarbonyl)amino group which is optionally substituted by $R^a$, and when the number of substituents is two or more, the respective substituents are the same or different, $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_{2-6}$ haloalkynylsulfonyl group, a nitro group, a cyano group, a formyl group, a hydroxy group, a mercapto group, an amino group, SCN, a $C_{1-6}$ alkyloxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di$C_{1-6}$ alkylamino group, the number of substituents $R^a$ is from 1 to 5, and when the number of $R^a$ is two or more, the respective substituents are the same or different, each of $R^2$ and $R^3$ which are independent of each other, is a hydrogen atom or a $C_{1-6}$ alkyl group, and Ar is an aryl group which is optionally substituted by $R^a$, with a halogenating agent to produce a 2-azaadamantane carbamate compound of formula (2):

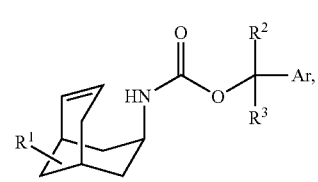

(2)

wherein X is a halogen atom; and (B) subjecting the 2-azaadamantane carbamate compound to hydrogenolysis, to obtain the compound of formula (3)

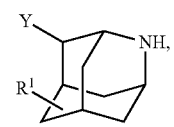

(3)

wherein Y is a hydrogen atom or a halogen atom, and wherein the halogenating agent comprises chlorine, bromine, iodine, N-chlorosuccinimide, N-bromosuccinimide, N-iodosuccinimide, 1,3-dibromo-5,5-dimethylhydantoin, thionyl chloride, sulfuryl chloride, or phosphorus oxychloride.

2. A method for producing a 2-azaadamantane carbamate compound of formula (2), the method comprising reacting with a halogenating agent a carbamate compound of formula (1):

(1)

wherein $R^1$ is at least one substituent selected from the group consisting of a hydrogen atom, a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a linear or branched $C_{1-12}$ alkylcarbonyl group, a $C_{3-12}$ cycloalkylcarbonyl group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a (linear or branched $C_{1-12}$ alkyl)carbonyloxy group, a ($C_{3-12}$ cycloalkyl)carbonyloxy group, a (linear or branched $C_{1-12}$ alkyl)carbonylthio group, a ($C_{3-12}$ cycloalkyl)carbonylthio group, a (linear or branched $C_{1-12}$ alkyl)carbonylamino group, a ($C_{3-12}$ cycloalkyl)carbonylamino group, a di(linear or branched $C_{1-12}$ alkylcarbonyl)amino group, a di($C_{3-12}$ cycloalkylcarbonyl)amino group, a linear or branched $C_{1-6}$ haloalkyl group, a $C_{3-6}$ halocycloalkyl group, a linear or branched $C_{2-6}$ alkenyl group, a $C_{3-6}$ cycloalkenyl group, a linear or branched $C_{2-6}$ haloalkenyl group, a $C_{3-6}$ halocycloalkenyl group, a linear or branched $C_{2-6}$ alkynyl group, a linear or branched $C_{2-6}$ haloalkynyl group, a benzyl group which is optionally substituted by $R^a$, a benzyloxy group which is optionally substituted by $R^a$, a benzylthio group which is optionally substituted by $R^a$, a benzylamino group which is optionally substituted by $R^a$, a dibenzylamino group which is optionally substituted by $R^a$, a benzylcarbonyl group which is optionally substituted by $R^a$, a benzyloxycarbonyl group which is optionally substituted by $R^a$, a benzylthiocarbonyl group which is optionally substituted by $R^a$, a benzylaminocarbonyl group which is optionally substituted by $R^a$, a dibenzylaminocarbonyl group which is optionally substituted by $R^a$, a benzylcarbonyloxy group which is optionally substituted by $R^a$, a benzylcarbonylthio group which is optionally substituted by $R^a$, a benzylcarbonylamino group which is optionally substituted by $R^a$, a di(benzylcarbonyl)amino group which is optionally substituted by $R^a$, an aryl group which is optionally substituted by $R^a$, an aryloxy group which is optionally substituted by $R^a$, an arylthio group which is optionally substituted by $R^a$, an arylamino group which is optionally substituted by $R^a$, a diarylamino group which is optionally substituted by $R^a$, an arylcarbonyl group which is optionally substituted by $R^a$, an aryloxycarbonyl group which is optionally substituted by $R^a$, an arylthiocarbonyl group which is optionally substituted by $R^a$, an arylaminocarbonyl group which is optionally substituted by $R^a$, a diarylaminocarbonyl group which is optionally substituted by $R^a$, an arylcarbonyloxy group which is optionally substituted by $R^a$, an arylcarbonylthio group which is optionally substituted by $R^a$, an arylcarbonylamino group which is optionally substituted by $R^a$, and a di(arylcarbonyl)amino group which is optionally substituted by $R^a$, and when the number of substituents is two or more, the respective substituents are the same or different, $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a C haloalkynylsulfonyl group, a nitro group, a cyano group, a formyl group, a hydroxy group, a mercapto group, an amino group, SCN, a $C_{1-6}$ alkyloxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di$C_{1-6}$ alkylamino group, the number of substituents $R^a$ is from 1 to 5, and when the number of $R^a$ is two or more, the respective substituents are the same or different, each of $R^2$ and $R^3$ which are independent of each other, is a hydrogen atom or a $C_{1-6}$ alkyl group, and Ar is an aryl group which is optionally substituted by $R^a$, to obtain the compound of formula (2)

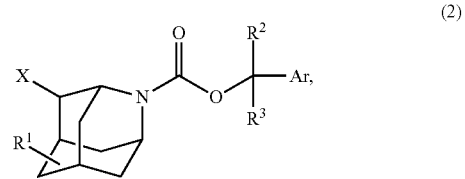

(2)

wherein X is a halogen atom, wherein the halogenating agent comprises chlorine, bromine, iodine, N-chlorosuccinimide, N-bromosuccinimide, N-iodosuccinimide, 1,3-dibromo-5,5-dimethylhydantoin, thionyl chloride, sulfuryl chloride, or phosphorus oxychloride.

3. A method for producing a 2-azaadamantane compound of formula (3) or its salt, the method comprising subjecting a 2-azaadamantane carbamate compound of formula (2)

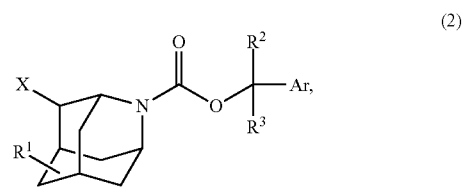

(2)

wherein $R^1$ is at least one substituent selected from the group consisting of a hydrogen atom, a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a linear or branched $C_{1-12}$ alkylcarbonyl group, a $C_{3-12}$ cycloalkylcarbonyl group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a (linear or branched $C_{1-12}$ alkyl)carbonyloxy group, a ($C_{3-12}$ cycloalkyl)carbonyloxy group, a (linear or branched $C_{1-12}$ alkyl)carbonylthio group, a ($C_{3-12}$ cycloalkyl)carbonylthio group, a (linear or branched $C_{1-12}$ alkyl)carbonylamino group, a ($C_{3-12}$ cycloalkyl)carbonylamino group, a di(linear or branched $C_{1-12}$ alkylcarbonyl)amino group, a di($C_{3-12}$ cycloalkylcarbonyl)amino group, a linear or branched $C_{1-6}$ haloalkyl group, a $C_{3-6}$ halocycloalkyl group, a linear or branched $C_{2-6}$ alkenyl group, a $C_{3-6}$ cycloalkenyl group, a linear or branched $C_{2-6}$ haloalkenyl group, a $C_{3-6}$ halocycloalkenyl group, a linear or branched $C_{2-6}$ alkynyl group, a linear or branched $C_{2-6}$ haloalkynyl group, a benzyl group which is optionally substituted by $R^a$, a benzyloxy group which is optionally substituted by $R^a$, a benzylthio group which is optionally substituted by $R^a$, a benzylamino group which is optionally substituted by $R^a$, a dibenzylamino group which is optionally substituted by $R^a$, a benzylcarbonyl group which is optionally substituted by $R^a$, a benzyloxycarbonyl group which is optionally substituted by $R^a$, a benzylthiocarbonyl group which is optionally substituted by $R^a$, a benzylaminocarbonyl group which is optionally substituted by $R^a$, a dibenzylaminocarbonyl group which is optionally substituted by $R^a$, a benzylcarbonyloxy group which is optionally substituted by $R^a$, a benzylcarbonylthio group which is optionally substituted by $R^a$, a benzylcarbonylamino group which is optionally substituted by $R^a$, a di(benzylcarbonyl)amino group which is optionally substituted by $R^a$, an aryl group which is optionally substituted by $R^a$, an aryloxy group which is optionally substituted by $R^a$, an arylthio group which is optionally substituted by $R^a$, an arylamino group which is optionally substituted by $R^a$, a diarylamino group which is optionally substituted by $R^a$, an arylcarbonyl group which is optionally substituted by $R^a$, an aryloxycarbonyl group which is optionally substituted by $R^a$, an arylthiocarbonyl group which is optionally substituted by $R^a$, an arylaminocarbonyl group which is optionally substituted by $R^a$, a diarylaminocarbonyl group which is optionally substituted by $R^a$, an arylcarbonyloxy group which is optionally substituted by $R^a$, an arylcarbonylthio group which is optionally substituted by $R^a$, an arylcarbonylamino group which is optionally substituted by $R^a$, and a di(arylcarbonyl)amino group which is optionally substituted by $R^a$, and when the number of substituents is two or more, the respective substituents are the same or different, $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_{2-6}$ haloalkynylsulfonyl group, a nitro group, a cyano group, a formyl group, a hydroxy group, a mercapto group, an amino group, SCN, a $C_{1-6}$ alkyloxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di$C_{1-6}$ alkylamino group, the number of substituents $R^a$ is from 1 to 5, and when the number of $R^a$ is two or more, the respective substituents are the same or different, and each of $R^2$ and $R^3$ which are independent of each other, is a hydrogen atom or a $C_{1-6}$ alkyl group, X is a halogen atom, and Ar is an aryl group which is optionally substituted by $R^a$, to hydrogenolysis, to obtain the compound of formula (3)

wherein Y is a halogen atom or a hydrogen atom.

4. The method of claim 1, wherein $R^1$ is at least one substituent selected from the group consisting of a hydrogen atom, a hydroxy group, an amino group, a linear or branched $C_{1-12}$ alkyl group, a $C_{3-12}$ cycloalkyl group, a (linear or branched $C_{1-12}$ alkyl)oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3-12}$ cycloalkyl)aminocarbonyl group, a di(linear or branched $C_{1-6}$ alkyl)aminocarbonyl group, a di($C_{3-6}$ cycloalkyl)aminocarbonyl group, a benzyl group which is optionally substituted by $R^a$, an aryl group which is optionally substituted by $R^a$, an aryloxy group which is optionally substituted by $R^a$, an arylthio group which is optionally substituted by $R^a$, an arylamino group which is optionally substituted by $R^a$, and a diarylamino group which is optionally substituted by $R^a$, and when the number of substituents is two or more, the respective substituents are the same or different; and $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a hydroxy group, an amino group, a phenyl group, a $C_{1-6}$ alkylamino group or a di$C_{1-6}$ alkylamino group, the number of substituents $R^a$ is from 1 to 5, and when the number of $R^a$ is two or more, the respective substituents are the same or different.

5. The method of claim 1, wherein $R^1$ is a hydrogen atom.

6. A 2-azaadamantane carbamate compound of formula (2):

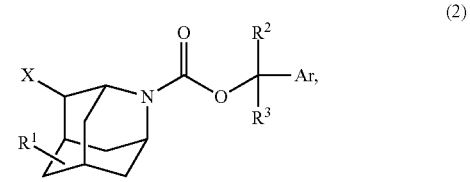

wherein $R^1$ is at least one substituent selected from the group consisting of a hydrogen atom, a halogen atom, a nitro group, a cyano group, a hydroxy group, a mercapto group, an amino group, a formyl group, a carboxy group, a sulfo group, a linear or branched $C_{1-12}$ alkyl group, a $C_{3-12}$ cycloalkyl group, a (linear or branched $C_{1-12}$ alkyl) oxy group, a ($C_{3-12}$ cycloalkyl)oxy group, a (linear or branched $C_{1-12}$ alkyl)thio group, a ($C_{3-12}$ cycloalkyl)thio group, a (linear or branched $C_{1-12}$ alkyl)amino group, a ($C_{3-12}$ cycloalkyl)amino group, a di(linear or branched $C_{1-6}$ alkyl)amino group, a di($C_{3-6}$ cycloalkyl)amino group, a linear or branched $C_{1-12}$ alkylcarbonyl group, a $C_{3-12}$ cycloalkylcarbonyl group, a (linear or branched $C_{1-12}$ alkyl)oxycarbonyl group, a ($C_{3-12}$ cycloalkyl)oxycarbonyl group, a (linear or branched $C_{1-12}$ alkyl)thiocarbonyl group, a ($C_{3-12}$ cycloalkyl)thiocarbonyl group, a (linear or branched $C_{1-12}$ alkyl)aminocarbonyl group, a ($C_{3,12}$ cycloalkyl)aminocarbonyl group, a di(linear or branched $C_{1-6}$ alkyl)aminocarbonyl group, a di($C_{3-6}$ cycloalkyl)aminocarbonyl group, a (linear or branched $C_{1-12}$ alkyl)carbonyloxy group, a ($C_{3-12}$ cycloalkyl)carbonyloxy group, a (linear or branched $C_{1-12}$ alkyl)carbonylthio group, a ($C_{3-12}$ cycloalkyl)carbonylthio group, a (linear or branched $C_{1-12}$ alkyl)carbonylamino group, a ($C_{3-12}$ cycloalkyl)carbonylamino group, a di(linear or branched $C_{1-12}$ alkylcarbonyl)amino group, a di($C_{3-12}$ cycloalkylcarbonyl)amino group, a linear or branched $C_{1-6}$ haloalkyl group, a $C_{3-6}$ halocycloalkyl group, a linear or branched $C_{2-6}$ alkenyl group, a $C_{3-6}$ cycloalkenyl group, a linear or branched $C_{2-6}$ haloalkenyl group, a $C_{3-6}$ halocycloalkenyl group, a linear or branched $C_{2-6}$ alkynyl group, a linear or branched $C_{2-6}$ haloalkynyl group, a benzyl group which is optionally substituted by $R^a$, a benzyloxy group which is optionally substituted by $R^a$, a benzylthio group which is optionally substituted by $R^a$, a benzylamino group which is optionally substituted by $R^a$, a dibenzylamino group which is optionally substituted by $R^a$, a benzylcarbonyl group which is optionally substituted by $R^a$, a benzyloxycarbonyl group which is optionally substituted by $R^a$, a benzylthiocarbonyl group which is optionally substituted by $R^a$, a benzylaminocarbonyl group which is optionally substituted by $R^a$, a dibenzylaminocarbonyl group which is optionally substituted by $R^a$, a benzylcarbonyloxy group which is optionally substituted by $R^a$, a benzylcarbonylthio group which is optionally substituted by $R^a$, a benzylcarbonylamino group which is optionally substituted by $R^a$, a di(benzylcarbonyl)amino group which is optionally substituted by $R^a$, an aryl group which is optionally substituted by $R^a$, an aryloxy group which is optionally substituted by $R^a$, an arylthio group which is optionally substituted by $R^a$, an arylamino group which is optionally substituted by $R^a$, a diarylamino group which is optionally substituted by $R^a$, an arylcarbonyl group which is optionally substituted by $R^a$, an aryloxycarbonyl group which is optionally substituted by $R^a$, an arylthiocarbonyl group which is optionally substituted by $R^a$, an arylaminocarbonyl group which is optionally substituted by $R^a$, a diarylaminocarbonyl group which is optionally substituted by $R^a$, an arylcarbonyloxy group which is optionally substituted by $R^a$, an arylcarbonylthio group which is optionally substituted by $R^a$, an arylcarbonylamino group which is optionally substituted by $R^a$, and a di(arylcarbonyl)amino group which is optionally substituted by $R^a$, and when the number of substituents is two or more, the respective substituents are the same or different, $R^a$ is a halogen atom, a $C_{1-6}$ alkyl group, a $C_{1-6}$ haloalkyl group, a $C_{3-6}$ cycloalkyl group, a $C_{1-6}$ alkoxy group, a $C_{1-6}$ alkoxy $C_{1-6}$ alkyl group, a $C_{1-6}$ alkylsulfenyl $C_{1-6}$ alkyl group, a $C_{1-6}$ haloalkoxy group, a $C_{1-6}$ alkylsulfenyl group, a $C_{1-6}$ alkylsulfinyl group, a $C_{1-6}$ alkylsulfonyl group, a $C_{1-6}$ haloalkylsulfenyl group, a $C_{1-6}$ haloalkylsulfinyl group, a $C_{1-6}$ haloalkylsulfonyl group, a $C_{2-6}$ alkenyl group, a $C_{2-6}$ haloalkenyl group, a $C_{2-6}$ alkenyloxy group, a $C_{2-6}$ haloalkenyloxy group, a $C_{2-6}$ alkenylsulfenyl group, a $C_{2-6}$ alkenylsulfinyl group, a $C_{2-6}$ alkenylsulfonyl group, a $C_{2-6}$ haloalkenylsulfenyl group, a $C_{2-6}$ haloalkenylsulfinyl group, a $C_{2-6}$ haloalkenylsulfonyl group, a $C_{2-6}$ alkynyl group, a $C_{2-6}$ haloalkynyl group, a $C_{2-6}$ alkynyloxy group, a $C_{2-6}$ haloalkynyloxy group, a $C_{2-6}$ alkynylsulfenyl group, a $C_{2-6}$ alkynylsulfinyl group, a $C_{2-6}$ alkynylsulfonyl group, a $C_{2-6}$ haloalkynylsulfenyl group, a $C_{2-6}$ haloalkynylsulfinyl group, a $C_{2-6}$ haloalkynylsulfonyl group, a nitro group, a cyano group, a formyl group, a hydroxy group, a mercapto group, an amino group, SCN, a $C_{1-6}$ alkyloxycarbonyl group, a $C_{1-6}$ alkylcarbonyl group, a $C_{1-6}$ haloalkylcarbonyl group, a $C_{1-6}$ alkylcarbonyloxy group, a phenyl group, a $C_{1-6}$ alkylamino group or a di$C_{1-6}$ alkylamino group, the number of substituents $R^a$ is from 1 to 5, and when the number of $R^a$ is two or more, the respective substituents are the same or different, and each of $R^2$ and $R^3$ which are independent of each other, is a hydrogen atom or a $C_{1-6}$ alkyl group, Ar is an aryl group which is optionally substituted by $R^a$, and X is a halogen atom.

7. The compound of claim 6, wherein $R^1$ is a hydrogen atom.

8. The method of claim 2, wherein $R^1$ is a hydrogen atom.

9. The method of claim 3, wherein $R^1$ is a hydrogen atom.

10. The method of claim 1, wherein $R^1$ is a halogen atom, a nitro group, or a cyano group.

11. The method of claim 1, wherein $R^1$ is a hydroxy group.

12. The method of claim 1, wherein $R^1$ is a mercapto group.

13. The method of claim 1, wherein $R^1$ is an amino group.

14. The method of claim 1, wherein $R^1$ is a formyl group.

15. The method of claim 1, wherein $R^1$ is a carboxy group.

16. The method of claim 1, wherein $R^1$ is a (linear or branched $C_{1-12}$ alkyl)amino group.

17. The method of claim 1, wherein $R^1$ is a linear or branched $C_{1-12}$ alkyl group.

18. The method of claim 1, wherein $R^1$ is a $C_{3-12}$ cycloalkyl group.

19. The method of claim 1, further comprising:

reacting a compound of formula (0)

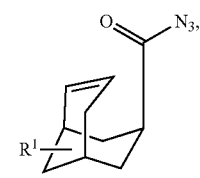

in the presence of a reactant comprising an alcohol, to directly obtain the compound of formula (1).

20. The method of claim 2, further comprising:

reacting a compound of formula (0)

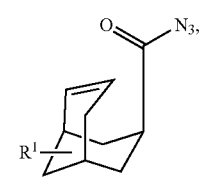

in the presence of a reactant comprising an alcohol, to directly obtain the compound of formula (1).

* * * * *